(12) United States Patent
Froggatt et al.

(10) Patent No.: US 7,772,541 B2
(45) Date of Patent: Aug. 10, 2010

(54) FIBER OPTIC POSITION AND/OR SHAPE SENSING BASED ON RAYLEIGH SCATTER

(75) Inventors: Mark E. Froggatt, Blacksburg, VA (US); Roger G. Duncan, Christianburg, VA (US)

(73) Assignee: Luna Innnovations Incorporated, Roanoke, VA (US)

( * ) Notice: Subject to any disclaimer, the term of this patent is extended or adjusted under 35 U.S.C. 154(b) by 0 days.

(21) Appl. No.: 12/047,056

(22) Filed: Mar. 12, 2008

(65) Prior Publication Data

US 2008/0212082 A1 Sep. 4, 2008

Related U.S. Application Data

(63) Continuation-in-part of application No. 11/535,438, filed on Sep. 26, 2006, which is a continuation-in-part of application No. 11/180,389, filed on Jul. 13, 2005, now abandoned.

(60) Provisional application No. 60/907,031, filed on Mar. 16, 2007, provisional application No. 60/588,336, filed on Jul. 16, 2004.

(51) Int. Cl.
*G01N 21/25* (2006.01)
*G01J 3/50* (2006.01)

(52) U.S. Cl. ................... 250/227.23; 250/226

(58) Field of Classification Search ................ 250/221, 250/227.14–227.19, 227.23; 356/73.1, 35, 356/35.5, 301–303; 385/12, 13, 123, 124, 385/126; 340/540, 541, 545.3, 552, 555–557
See application file for complete search history.

(56) References Cited

U.S. PATENT DOCUMENTS

| 4,295,738 | A |  | 10/1981 | Meltz et al. |
| 4,443,698 | A |  | 4/1984 | Schiffner |
| 5,317,147 | A |  | 5/1994 | Dandliker et al. |
| 5,563,967 | A |  | 10/1996 | Haake |
| 5,633,494 | A | * | 5/1997 | Danisch ............ 250/227.16 |
| 5,798,521 | A | * | 8/1998 | Froggatt ............ 250/227.19 |

(Continued)

FOREIGN PATENT DOCUMENTS

WO   WO 2007/109778   9/2007

(Continued)

OTHER PUBLICATIONS

U.S. Appl. No. 11/535,438, filed Sep. 26, 2006, Childers.

(Continued)

*Primary Examiner*—Que T Le
*Assistant Examiner*—Pascal M Bui-Pho
(74) *Attorney, Agent, or Firm*—Nixon & Vanderhye P.C.

(57) ABSTRACT

A fiber optic position and/or shape sensing device includes an optical fiber with either two or more single core optical fibers or a multi-core optical fiber having two or more fiber cores. In either case, the fiber cores are spaced apart so that mode coupling between the fiber cores is reduced, and preferably, minimized. The optical fiber is physically associated with an object. Strain on at least a portion of the optical fiber where it is associated with the object is determined by an OFDR using one or more Rayleigh scatter patterns for that portion of the optical fiber. The determined strain is used to determine a position and/or a shape of the object.

35 Claims, 14 Drawing Sheets

U.S. PATENT DOCUMENTS

| | | | |
|---|---|---|---|
| 5,930,435 | A * | 7/1999 | Laming et al. ............ 385/126 |
| 6,097,488 | A | 8/2000 | Grek et al. |
| 6,154,594 | A | 11/2000 | Fiacco et al. |
| 6,160,943 | A | 12/2000 | Davis et al. |
| 6,229,599 | B1 | 5/2001 | Galtarossa |
| 6,256,090 | B1 | 7/2001 | Chen et al. |
| 6,301,420 | B1 | 10/2001 | Greenaway et al. |
| 6,389,187 | B1 | 5/2002 | Greenaway et al. |
| 6,426,496 | B1 | 7/2002 | Froggatt et al. |
| 6,470,205 | B2 | 10/2002 | Bosselmann et al. |
| 6,471,710 | B1 | 10/2002 | Buckholz |
| 6,545,760 | B1 | 4/2003 | Froggatt et al. |
| 6,606,148 | B2 * | 8/2003 | Fredin et al. ............... 356/73.1 |
| 6,876,786 | B2 * | 4/2005 | Chliaguine et al. ............ 385/13 |
| 6,878,926 | B2 | 4/2005 | Martinez et al. |
| 6,888,623 | B2 | 5/2005 | Clements |
| 6,946,646 | B2 | 9/2005 | Chen et al. |
| 7,003,184 | B2 | 2/2006 | Ronnekleiv et al. |
| 7,126,678 | B2 | 10/2006 | Fayolle et al. |
| 7,324,714 | B1 | 1/2008 | Cranch et al. |
| 7,330,245 | B2 | 2/2008 | Froggatt |
| 7,424,193 | B2 | 9/2008 | Galvanauskas |
| 7,440,087 | B2 | 10/2008 | Froggatt et al. |
| 2002/0159134 | A1 | 10/2002 | Ghera et al. |
| 2006/0013523 | A1 | 1/2006 | Childers et al. |
| 2007/0012872 | A1 | 1/2007 | Poland et al. |
| 2007/0032723 | A1 | 2/2007 | Glossop |
| 2007/0060847 | A1 | 3/2007 | Leo et al. |
| 2007/0151391 | A1 | 7/2007 | Larkin et al. |
| 2007/0156019 | A1 | 7/2007 | Larkin et al. |
| 2007/0201793 | A1 | 8/2007 | Askins et al. |

OTHER PUBLICATIONS

U.S. Appl. No. 11/180,389, filed Jul. 13, 2005, Childers.
U.S. Appl. No. 11/062,740, filed Feb. 23, 2005, Inventor: Froggatt.
U.S. Appl. No. 11/371,229, filed Mar. 9, 2006; Inventor: Froggatt.
U.S. Appl. No. 11/808,260, filed Jun. 7, 2007; Inventor: Froggatt.
International Search Report and Written Opinion mailed Jun. 24, 2008 in corresponding PCT Application PCT/US08/03236.
Huttner et al., "Local Birefringence Measurements in Single-Mode Fibers with Coherent Optical Frequency-Domain Reflectometer", IEEE Photonics Technology Letters, vol. 10, No. 10, Oct. 1998.
Limberger et al., "OLCR Characterization of Efficient Bragg Gratings in Optical Fiber", SPIE vol. 2044, pp. 272-283.
Wayne V. Sorin, "High Resolution Optical Fiber Reflectometry Techniques", SPIE vol. 1797 Distributed and Multiplexed Fiber Optic Sensors II (1992); pp. 109-118.
Duncan, R. et al., "Characterization of a Fiber-Optic Shape and Position Sensor," SPIE International Symposium on Smart Structures and Materials, Proc. SPIE 6167-4 (2006).
Duncan, R. et al., "Fiber-Optic Shape and Position Sensing," Proceedings of the 5$^{th}$ International Conference on Structural Health Monitoring (2005).
Duncan, R. et al., "Use of a Fiber-Optic Distributed Sensing System for Nondestructive Testing of Aerospace Structures," Materials Evaluation 61, 838 (2003).
Duncan, R. et al., "A Distributed Sensing Technique for Aerospace Applications," 42$^{nd}$ AIAA Aerospace Sciences Meeting (2004), pp. 1-8.

Duncan, R. et al., "High-Accuracy Fiber-Optic Shape Sensing," SPIE International Symposium on Smart Structures and Materials, Proc. SPIE 6530-650 (2007).
Duncan, R., Sensing Shape, SPIE's OEMagazine, Sep. 2005, pp. 18-21, vol. 5, No. 8, SPIE, US.
Froggatt, M., "Distributed Measurement of the Complex Modulation of a Photoinduced Bragg Grating in an Optical Fiber," Appl. Opt. 35, No. 25, pp. 5162-5164 (Sep. 1, 1996).
Froggatt, M. et al., "Distributed Measurement of Static Strain in an Optical Fiber with Multiple Bragg Gratings at Nominally Equal Wavelengths," Applied Optics vol. 27, No. 10, pp. 1741-1746 (Apr. 1, 1998).
Froggatt, M. et al., "Correlation and Keying of Rayleigh Scatter for Loss and Temperature Sensing in Parallel Optical Networks," OFC Technical Digest, paper PDP 17, 2004.
Froggatt et al., "Distributed Strain and Temperature Discrimination in Unaltered Polarization Maintaining Fiber," Optical Fiber Sensors, OSA Technical Digest (CD), Optical Society of America, 2006, paper ThC5.
Eickoff, W. et al., "Optical Frequency Domain Reflectometry in single-Mode Fiber," Appl. Phys. Lett. 39 (9), 693-695, Nov. 1, 1981.
Childers, B. et al., "Recent Developments in the Application of Optical Frequency Domain Reflectometry to Distributed Bragg Grating Sensing," Fiber Optic Sensor Technology and Applications 2001, Proc. SPIE 4578 (2001), pp. 19-31.
Childers, B. et al., "Use of 3000 Bragg Grating Strain Sensors Distributed on Four Eight-Meter Optical Fibers During Static Load Tests of a Composite Structure," Smart Structures and Materials Conference, Proc. SPIE vol. 4332 (2001), pp. 133-142.
Kreger, S. et al., "High Resolution Distributed Strain or Temperature Measurements in Single- and Multi-mode Fiber Using Swept-Wavelength Interferometry," OFS 18 Technical Digest, Cancun, Mexico, Oct. 2006, paper ThE42.
Kreger, S. et al., "Return Loss Measurement in the Presence of Variable Insertion Loss Using Optical Frequency Domain Reflectometry", NIST Symposium for Photonic and Fiber Measurements, Sep. 19, 2006.
Kersey, Alan et al., "Fiber Grating Sensors," Journal of Lightwave Technology, Aug. 1997, vol. 15, No. 8, pp. 1442-1463.
Blanchard, P.M. et al., Two-Dimensional Bend Sensing with a Single, Multi-Core Optical Fibre, Smart Mater. Struct., vol. 9, 2000, pp. 132-140.
Sang et al., "High-Resolution Extended Distance Distributed Strain Measurements Using Swept-Wavelength Interferometry", Proceedings of EPRI's 3$^{rd}$ Increased Power Flow Conference (Aug. 2006).
Sorin, High Resolution Optical Fiber Reflectometry Techniques, SPIE vol. 1797 Distributed and Multiplexed Fiber Optic Sensors II (1992), pp. 109-118.
Limberger et al., "OLCR Characterization of Efficient Bragg Gratings in Optical Fiber", SPIE vol. 2044, Aug. 17, 1993, pp. 272-283.
U.S. Appl. No. 11/535,438, filed Sep. 26, 2006; Inventor: Childers et al.
Froggatt, M. et al., "High Resolution Strain Measurement in Optical Fiber with Rayleigh Scatter," Appl. Opt., 37, 1735-1740, Apr. 1, 1998.
Transmittal of International Preliminary Report on Patentability mailed Oct. 1, 2009 in corresponding PCT Application No. PCT/US2008/003236.

* cited by examiner

FIBER OPTIC POSITION AND/OR SHAPE SENSING BASED ON RAYLEIGH SCATTER

PRIORITY CLAIMS

This application claims priority from U.S. provisional patent application Ser. No. 60/907,031, filed Mar. 16, 2007, the contents which are hereby incorporated by reference in their entirety. This application is also a continuation in part application of and claims priority from U.S. patent application Ser. No. 11/535,438, filed Sep. 26, 2006, which in turn is a continuation in part application of U.S. patent application Ser. No. 11/180,389, filed Jul. 13, 2005, now abandoned, that claims priority from U.S. provisional patent application Ser. No. 60/588,336, filed Jul. 16, 2004, the contents all of which are hereby incorporated by reference in their entirety.

REFERENCE TO RELATED APPLICATION

This application is related to commonly-assigned U.S. patent application Ser. No. 11/062,740, to Froggatt et al. entitled "Identifying Optical Fiber Segments and Determining Characteristics of an Optical Device Under Test Based on Fiber Segment Scatter Pattern Data."

STATEMENT REGARDING FEDERALLY SPONSORED RESEARCH OR DEVELOPMENT

This application is related to work performed under government funding from Sandia Corporation SF 6432-FP (12-04) Document #509717.

TECHNICAL FIELD

The technical field relates to relates to fiber optic sensing.

BACKGROUND

Fiber optic strain sensors are used in applications such as smart structures and health monitoring. The advantages of these sensors include their small size, low cost, multiplexing capabilities, immunity to electromagnetic interference, intrinsic safety and their capability to be embedded into structures.

Many structural devices and objects undergo various shape changes when exposed to certain environments. In some instances, it is necessary to know the degree of change and to compensate for these changes. By embedding or attaching a sensor to the structure, one can monitor the dynamic shape or relative position of the structure independently from temperature or load effects. Further by measuring the dynamic shape of a structure, the state of flexible structures can be established. When a degradation of the measured signal occurs, it can be corrected using signal processing.

Some have tried to measure shape changes by using foil strain gauges. These sensors, while sufficient for making local bend measurements, are impractical for use with sufficient spatial resolution to reconstruct shape or relative position over all but the smallest of distances. Others have used fiber optic micro-bend sensors to measure shape. This approach relies on losses in the optical fiber which cannot be controlled in real-world applications.

Clements (U.S. Pat. No. 6,888,623 B2) describes a fiber optic sensor for 3-D position measurement. The central system component of the invention is a flexible "smart cable" which enables measurement of local curvature and torsion along its length. These quantities are used to infer the position and attitude of one end of the cable relative to the other. Measurements of the local curvature and torsion along the cable allow reconstruction of the entire cable shape, including the relative position and orientation of the end points. The smart cable for making these measurements comprises a multicore optical fiber, with individual fiber cores constructed to operate in the single mode regime, but positioned close enough to cause cross-talk (mode coupling) between cores over the length of the fiber. This cross-talk is very sensitive to the distribution of strain (curvature and torsion) along the cable. Clements describes the errors in measured curvature as being divided into three classes: those due to instrument noise, systematic errors due to fabrication defects (core geometry, index of refraction variations, etc.), and sensitivity to extrinsic variables such as temperature. Of the three, instrument noise is probably the worst threat to successful shape inversion. Several approaches are proposed to mitigating effects of instrument noise, including time averaging and diversity measurements using fibers with redundant cores or multiple multicore fibers. A plurality of single mode cores may also be provided in an optical medium comprising a flexible sheet of material.

Greenaway et al. (U.S. Pat. No. 6,301,420 B1) describe a multicore optical fiber for transmitting radiation. The optical fiber comprises two or more core regions, each core region comprising a substantially transparent core material and having a core refractive index, a core length, and a core diameter. The core regions are arranged within a cladding region. The cladding region comprises a length of first substantially transparent cladding material having a first refractive index. The first substantially transparent cladding material has an array of lengths of a second cladding material embedded along its length. The second cladding material has a second refractive index which is less than the first refractive index, such that radiation input to the fiber propagates along at least one of the core regions. The cladding region and the core regions may be arranged such that radiation input to the optical fiber propagates along one or more of the lengths of the core regions in a single mode of propagation. The optical fiber may be used as a bend sensor, a spectral filter or a directional coupler. A bend sensor comprises a multicore photonic crystal fiber. The measurement of the relative shift in the fringe pattern provides an indication of the extent by which the fiber is bent. If the fiber is embedded in a structure, an indication of the extent to which the structure is bent is provided. This type of system is an intensity based system, in contrast to an internal reflection system, therefore not all light is guided by an internal reflection mode and, hence, the system is not as accurate as an internal reflection system.

Greenway et al. (U.S. Pat. No. 6,389,187 B1) describe an optical fiber bend sensor that measures the degree and orientation of bending present in a sensor length portion of a fiber assembly. Within a multicored fiber, cores are grouped in non-coplanar pairs. An arrangement of optical elements define within each core pair two optical paths which differ along the sensor length. One core of a pair is included in the first path and the other core in the second path. A general bending of the sensor region will lengthen one core with respect to the other. Interrogation of this length differential by means of interferometry generates interferograms from which the degree of bending in the plane of the core pair is extracted. Bend orientation can be deduced from data extracted from multiple core pairs. The apparatus is capable of determining bending of the sensor length, perhaps as a consequence of strain within an embedding structure, by monitoring that component of the bend in the plane of two fiber cores within the sensor length. Interferograms are formed between radiation propagating along two different optical paths, the optical paths differing within a specific region of the fiber. This region, the sensor length, may be only a fraction of the total fiber length. Generally, bending this sensing region will inevitably lengthen one core with respect to the other. Interrogation of this length differential by means of interferometry provides an accurate tool with which to measure bending. Moreover, defining a sensor length down a potentially long fiber downlead enables strains to be detected at a localized region remote from the radiation input end of the fiber. Thus, the fiber assembly can be incorporated in, for example, a building wall, and strains developing in the deep interior of the wall measured.

The first and second cores constitute a core pair and component cores of the multicore fiber preferably comprise an arrangement of such core pairs. The coupling means may accordingly be arranged to couple and reflect a portion of radiation propagating in the first core into the second core of the respective pair. This provides the advantage of flexibility. The optical path difference arising between any core pair can be interrogated, enabling the selection of planes any of which may be the plane in which components of a general bend curvature may be measured.

Schiffner (U.S. Pat. No. 4,443,698) describes a sensing device having a multicore optical fiber as a sensing element. The sensing device includes a sensing element in the form of an optical fiber, a device for coupling light into the fiber and a device for measuring changes in the specific physical parameters of the light passing through the fiber to determine special physical influences applied to the fiber. The fiber is a multicore fiber having at least two adjacently extending cores surrounded by a common cladding and a means for measuring the alterations in the light passing through each of the cores. To make the device sensitive to bending and deformation in all directions, the fiber may have two cores and be twisted through 90 degrees or the fiber may have three or more cores which are not disposed in the same plane. The measuring of the amount of change may be by measuring the interference pattern from the superimposed beams of the output from the two cores or by measuring the intensity of each of the output beams separately. When there is no appreciable cross-coupling between the cores, an interferometric means for measurement will include a light receiving surface which is arranged in the path of light which passes through the two cores and has been brought into interference by means of superimposition. The sensing means may use a light receiving surface which is a collecting screen in which the interference pattern can be directly observed or the light receiving surface may be the light sensitive surface of a light sensitive detector which will monitor the light intensity of the interference pattern. To superimpose the light beams emitted from each of the cores, a beam divider device or devices may be utilized.

Haake (U.S. Pat. No. 5,563,967) describes a fiber optic sensor and associated sensing method including a multicore optical fiber having first and second optical cores adapted to transmit optical signals having first and second predetermined wavelengths, respectively, in a single spatial mode. The first and second optical cores each include respective Bragg gratings adapted to reflect optical signals having first and second predetermined wavelengths, respectively. Based upon the differences between the respective wavelengths of the optical signals reflected by the respective Bragg gratings and the first and second predetermined wavelengths, a predetermined physical phenomena to which the workpiece is subjected can be determined, independent of perturbations caused by other physical phenomena.

Froggatt and Moore, "Distributed Measurement of Static Strain in an Optical fiber with Multiple Bragg Gratings at Nominally Equal Wavelengths," Applied Optics, Vol. 27, No. 10, Apr. 1, 1998 describe a demodulation system to measure static strain in an optical fiber using multiple, weak, fiber Bragg gratings (FBGs) in a single fiber. Kersey et al. in "Fiber Grating Sensors," Journal of Lightwave Technology, Vol. 15, No. 8, August 1997 describe that a primary advantage of using FBGs for distributed sensing is that large numbers of sensors may be interrogated along a single fiber. With mixed WDM (wavelength division multiplexing)/TDM (time division multiplexing) in the serial configuration several wavelength-stepped arrays are concatenated, each at a greater distance along the fiber. Two deleterious effects can arise with strong reflectors. FBGs whose reflected light signals are separated in time, but which overlap in wavelength can experience cross-talk through "multiple-reflection" and "spectral-shadowing". The WDM/TDM parallel and branching optical fiber network topologies eliminate these deleterious effects, but at the price of reduced overall optical efficiency and the need for additional couplers and stronger FBGs.

Froggatt (U.S. Pat. No. 5,798,521) describes an apparatus and method for measuring strain in Bragg gratings. Optical radiation is transmitted over a plurality of contiguous predetermined wavelength ranges into a reference optical fiber network and an optical fiber network under test to produce a plurality of reference interference fringes and measurement interference fringes, respectively. The reference and measurement fringes are detected and sampled such that each sampled value of the reference and measurement fringes is associated with a corresponding sample number. The wavelength change of the reference optical fiber, for each sample number, due to the wavelength of the optical radiation is determined. Each determined wavelength change is matched with a corresponding sampled value of each measurement fringe. Each sampled measurement fringe of each wavelength sweep is transformed into a spatial domain waveform. The spatial domain waveforms are summed to form a summation spatial domain waveform that is used to determine location of each grating with respect to a reference reflector. A portion of each spatial domain waveform that corresponds to a particular grating is determined and transformed into a corresponding frequency spectrum representation. The strain on the grating at each wavelength of optical radiation is determined by determining the difference between the current wavelength and an earlier, zero-strain wavelength measurement.

Chen et al. (U.S. Pat. No. 6,256,090 B1) describe a method and apparatus for determining the shape of a flexible body. The device uses Bragg grating sensor technology and time, spatial, and wavelength division multiplexing, to produce a plurality of strain measurements along one fiber path. Using a plurality of fibers, shape determination of the body and the tow cable can be made with minimal ambiguity. The use of wavelength division multiplexing has its limitations in that the ability to have precision with respect to determining the shape and/or position of an object is limited. Wavelength division multiplexing can only be used with sensor arrays that have less than one hundred sensors and, therefore, is insufficient for the application of determining shape and or position of an object with any precision.

An object is to provide a fiber optic position and/or shape sensing device that employs an optical fiber comprising at least two fiber cores disposed therein coupled with a frequency domain reflectomer.

Another is to provide a method for determining position and/or shape of an object using the fiber optic position and shape sensing device.

SUMMARY

A fiber optic sensing device includes an optical fiber including at least two fiber cores spaced apart so that mode coupling between the fiber cores is reduced, and preferably minimized. Each fiber core has an associated Rayleigh scatter signature and different segments of each fiber core correspond to a portion of the associated Rayleigh scatter signature. A frequency domain reflectometer is coupled to the optical fiber for obtaining a Rayleigh scatter pattern associated with each of multiple fiber segments from each core. The Rayleigh scatter patterns are used to determine a strain parameter for each of the multiple fiber segments from each core. Based on the determined strain parameters, a position and/or shape of a portion of the fiber is(are) determined. In one non-limiting example implementation, the strain parameters are converted into local bend measurements defining a bend in the fiber at a particular location along the fiber which are integrated into a position or a shape.

The frequency domain reflectometer may detect a distributed strain field along a portion of each core including multiple segments based on the obtained Rayleigh scatter pattern associated with each of those fiber segments. In one non-limiting example implementation, the optical fiber includes at least two single core optical fibers, and the frequency domain reflectometer detects a distributed one-dimensional strain field along a portion of each of the two single core optical fibers including multiple segments based on the obtained Rayleigh scatter pattern associated with each of those fiber segments. In another non-limiting example implementation, the optical fiber includes three single core optical fibers that are non-coplanar and form a triangular shape. The frequency domain reflectometer detects a distributed strain field along a portion of each of the three single core optical fibers including multiple segments based on the obtained Rayleigh scatter pattern associated with each of those fiber segments. The three fiber cores each have a center, and in one non-limiting example implementation, each center is 120° with respect to each of the other two core centers.

A benefit of this technology is the ability to readily obtain many independent strain measurements along the length of the core. In one non-limiting example embodiment, at least one hundred Rayleigh scatter patterns along the length of each core are obtained.

In one non-limiting example implementation, the frequency domain reflectometer includes a broadband reference reflector. Rayleigh scatter patterns are obtained to establish an optical path length between the broadband reference reflector and the segments corresponding to the obtained Rayleigh scatter patterns. The optical frequency domain reflectometer may also be constructed with an internal optical reference path, and, therefore, not include a broadband reference reflector.

Depending on the application, the optical fiber may be disposed in, affixed to, coupled with, or conforming to at least a portion of an elongated body whose position and/or shape is to be determined. The elongate body could be a catheter, tube, pipe, sleeve, instrument, tool, wire, line, cavity, vessel, lumen, or conduit. The elongate body can be flexible.

A fiber optic method is also provided. A frequency domain reflectometer is coupled to an optical fiber having at least two fiber cores spaced apart so that mode coupling between the fiber cores is reduced. Each fiber core has an associated Rayleigh scatter signature and different segments of each fiber core correspond to a portion of the associated Rayleigh scatter signature. The optical fiber is physically associated with a position and/or shape of an object. The frequency domain reflectometer obtains a Rayleigh scatter pattern associated with each of multiple fiber segments from each core and uses the obtained Rayleigh scatter patterns to determine a strain parameter for each of the multiple fiber segments from each core, The position and/or shape of the object is(are) determined based on the determined strain parameters.

In another aspect, a medical instrument system is provided that includes a medical instrument and an optical fiber conforming to at least a portion of a shape the medical instrument and including at least two fiber cores spaced apart so that mode coupling between the fiber cores is reduced. Each fiber core has an associated Rayleigh scatter signature, and different segments of each fiber core correspond to a portion of the associated Rayleigh scatter signature. A frequency domain reflectometer coupled to the optical fiber obtains a Rayleigh scatter pattern associated with each of multiple fiber segments from each core and uses the obtained Rayleigh scatter patterns to determine a strain parameter of each of the multiple fiber segments from each core. A computing device determines a position and/or a shape of the portion of the medical instrument based on the determined strain parameters.

DETAILED DESCRIPTION

In the following description, for purposes of explanation and non-limitation, specific details are set forth, such as particular nodes, functional entities, techniques, protocols, standards, etc. in order to provide an understanding of the described technology. In other instances, detailed descriptions of well-known methods, devices, techniques, etc. are omitted so as not to obscure the description with unnecessary detail.

It will be appreciated by those skilled in the art that block diagrams herein can represent conceptual views of illustrative circuitry embodying the principles of the technology. Similarly, it will be appreciated that any flow charts, state transition diagrams, pseudocode, and the like represent various processes which may be embodied in computer readable medium and so executed by a computer or processor, whether or not such computer or processor is explicitly shown. The functions of the various elements including functional blocks may be provided through the use of dedicated electronic hardware as well as electronic circuitry capable of executing computer program instructions in association with appropriate software.

It will be apparent to one skilled in the art that other embodiments may be practiced apart from the specific details disclosed below. All statements reciting principles, aspects, and embodiments, as well as specific examples, are intended to encompass both structural and functional equivalents. Such equivalents include both currently known equivalents as well as equivalents developed in the future, i.e., any elements developed that perform the same function, regardless of structure.

The fiber optic position and/or shape sensing device generally comprises an optical fiber for determining position and shape of an object. The optical fiber comprises at least two fiber cores spaced apart from each other so that mode coupling between the fiber cores is reduced and preferably minimized. The device further comprises a frequency domain reflectometer that transmits light to and receives reflected light from the optical fiber. The optical fiber includes either at least two single core optical fibers positioned in a relative relationship to one another or a multicore optical fiber having at least two fiber cores.

Figure 1:
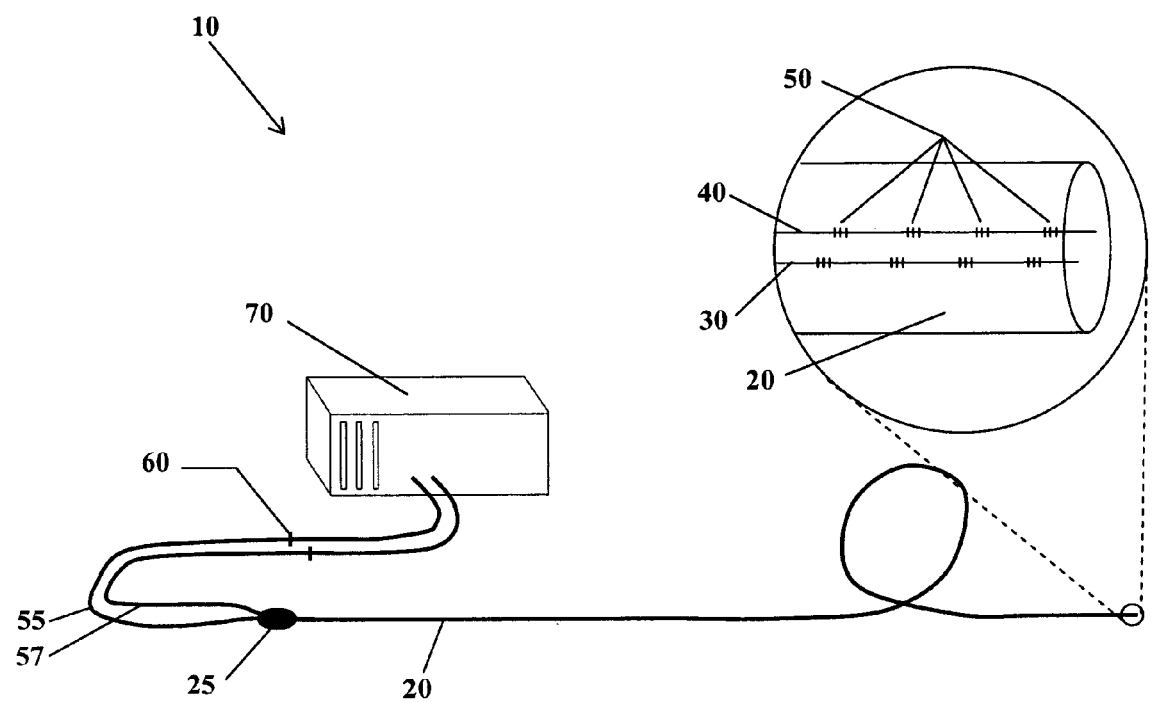
FIG. 1 is a schematic representation of a fiber optic position and/or shape sensing device having two fiber cores with Bragg gratings.
Figure 2:
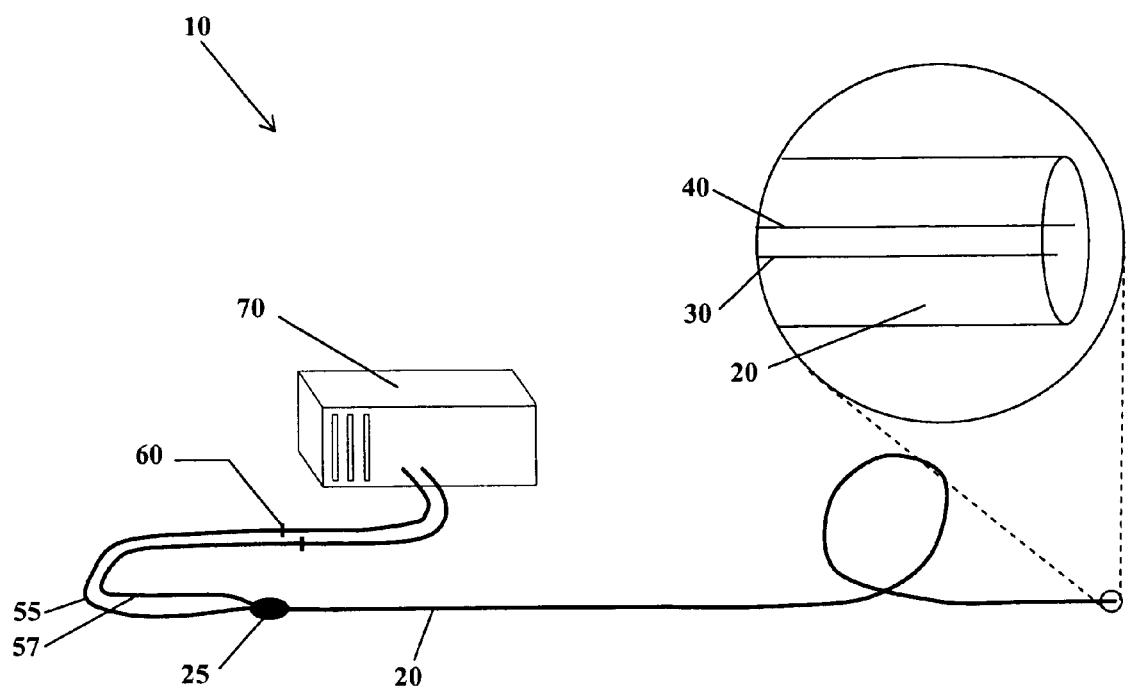
FIG. 2 is a schematic representation of a fiber optic position and/or shape sensing device having two fiber cores where the sensing mechanism is Rayleigh scatter rather than Bragg gratings.
Figure 3:
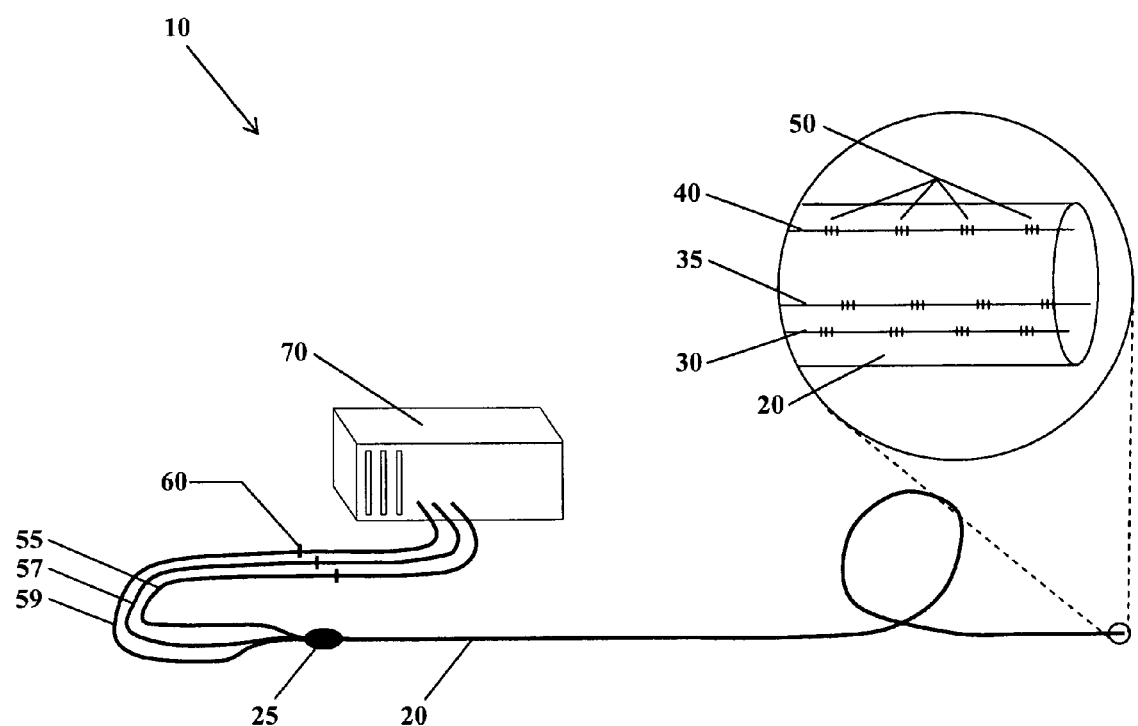
FIG. 3 is a schematic representation of a fiber optic position and/or shape sensing device having three fiber cores with Bragg gratings.
Figure 4:
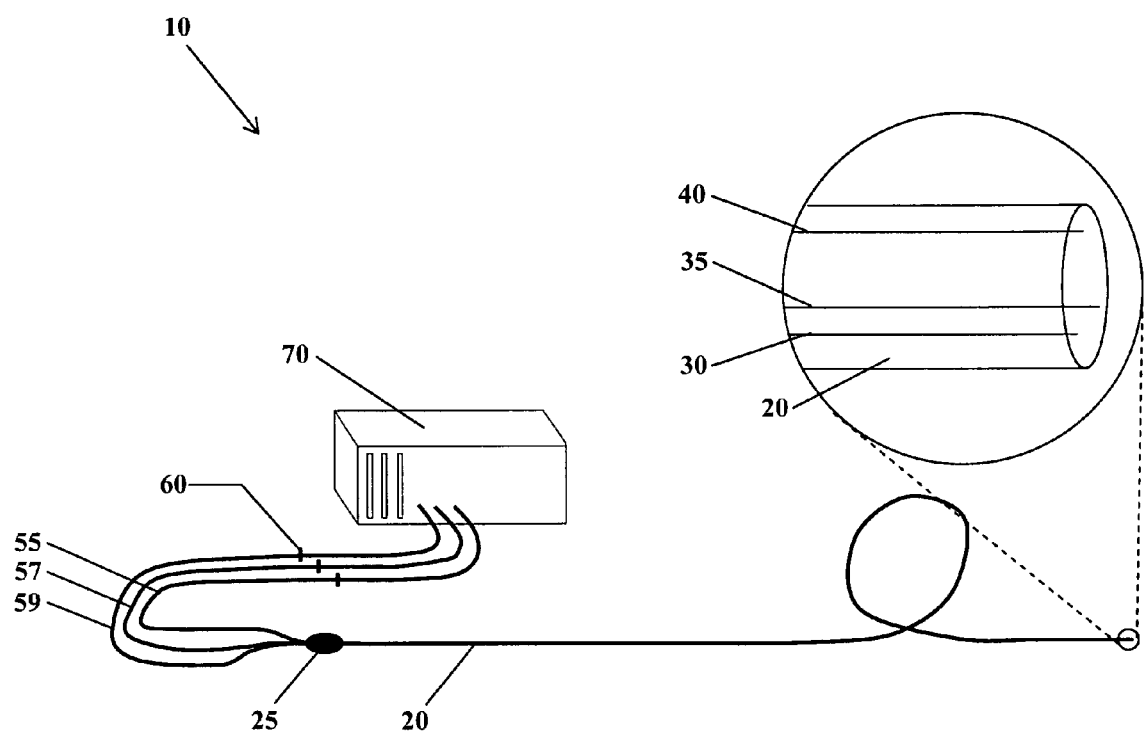
FIG. 4 is a schematic representation of a fiber optic position and/or shape sensing device having three fiber cores where the sensing mechanism is Rayleigh scatter rather than Bragg gratings.

Referring now to the figures where similar elements are numbered the same throughout, FIG. 1 depicts non-limiting example embodiment of a fiber optic position and/or shape sensing device 10. The optical fiber may be a multicore optical fiber 20 having at least two fiber cores 30, 40 spaced apart so that mode coupling between the fiber cores is reduced and preferably minimized or completely eliminated. Applicants have found that mode coupling causes distortions. A multicore optical fiber having two fiber cores (as depicted in FIGS. 1 and 2) is suitable for use as a positioning device or for determining the two dimensional shape of an object. When determining three dimensional shapes, the multicore optical fiber preferably includes three fiber cores 30, 35, 40 (as shown in FIGS. 3 and 4).

Multicore optical fiber is fabricated in much the same way as a standard telecommunications optical fiber. The first step in the fabrication process is to design and model the optical parameters for the preform (i.e., refractive index profile, core/cladding diameters, etc.) to obtain the desired waveguide performance. The fabrication of multi-core optical fiber requires the modification of standard over-cladding and fiberization processes. Though numerous methods can be employed to achieve the desired geometry, the preferred methods are the multi-chuck over-cladding procedure and the stack-and-draw process. In both techniques, the original preforms with the desired dopants and numerical aperture are fabricated via the Chemical Vapor Deposition (CVD) process. The preforms are then stretched to the appropriate diameters.

Following the preform stretch, the preforms are sectioned to the appropriate lengths and inserted into a silica tube with the other glass rods to fill the voids in the tube. The variation in the two procedures arises in the method in which the preform rods are inserted into the tube. In the multi-chuck method the bait rods and preforms are positioned in the tube on a glass working lathe. A double chuck is used to align the preforms in the tube. Once positioned, the tube is collapsed on the glass rods to form the preform. The preform is then fiberized in the draw tower by a standard procedure known to those of ordinary skill in the art. In the stack-and-draw process, the preforms and the bait rods are positioned together in the silica tube, with the interstitial space filled with additional glass rods. The glass assembly is then drawn into fiber with the appropriate dimensions.

In one non-limiting example embodiment, fiber Bragg gratings 50 may be disposed within and along each fiber core. In one preferred example, at least one hundred (100) fiber Bragg gratings. Each fiber Bragg grating is used to measure strain on the multi-core optical fiber. Fiber Bragg gratings are fabricated by exposing photosensitive fiber to a pattern of pulsed ultraviolet light from an excimer laser, that produces a periodic change in the refractive index of the core. This pattern, or grating, reflects a very narrow frequency band of light that is dependent upon the modulation period formed in the core. In its most basic operation as a sensor, a Bragg grating is either stretched or compressed by an external stimulus. This results in a change in the modulation period of the grating which, in turn, causes a shift in the frequency reflected by the grating. By measuring the shift in frequency, one can determine the magnitude of the external stimulus applied. However, Bragg gratings are not necessary.

An alternative and preferred way (other ways may be used) of measuring strain within an optical fiber uses the intrinsic Rayleigh scatter signature of the fiber. Rayleigh scatter in optical fiber is caused by random fluctuations in the index profile along the fiber length that are the result of minor imperfections in the fiber manufacturing process. For a given fiber, the scatter amplitude as a function of distance is a random but static property of that fiber and can be modeled as a long, weak fiber Bragg grating with a random period. Changes in the local period of the Rayleigh scatter caused by an external stimulus (like strain) in turn cause changes in the locally reflected spectrum. This spectral shift can then be calibrated to form a distributed strain sensor.

The Rayleigh scatter is interrogated similarly to Bragg gratings in that the complex reflection coefficient of a fiber as a function of wavelength is first obtained. The Rayleigh scatter as a function of length is obtained via the Fourier transform. A sensor is formed by first measuring and storing the Rayleigh scatter signature or profile of the fiber at a baseline state. The scatter profile is then measured when the fiber is in a perturbed state. The scatter profiles from the two data sets are then compared along the entire fiber length in increments of Δx. Each incremental fiber core segment represents a discrete sensing element, and can be considered a strain sensor. When a segment of fiber experiences a change in strain, the reflected spectrum from that segment shifts proportionally. To determine the amount of spectral shift, a complex cross-correlation is performed between reference data and measurement data for each fiber segment. Any change in strain manifests as a shift in the correlation peak. Therefore, to make a distributed strain measurement one simply measures the shift in the cross-correlation peak for each segment along the fiber. The Rayleigh scatter sensing mechanism was first described by Froggatt and Moore in "High spatial resolution distributed strain measurements in optical fiber using Rayleigh scatter," Applied Optics, Apr. 1, 1998 and "Apparatus and Method for Measuring Strain in Optical Fibers Using Rayleigh Scatter," U.S. Pat. No. 6,545,760, incorporated here by reference. See also commonly-assigned U.S. patent application Ser. No. 11/062,740 to Froggatt, incorporated here by reference.

Using Rayleigh scatter as a sensing mechanism has advantages. For example, not requiring Bragg gratings greatly reduces cost and increases availability of fiber. Also, the continuous nature of the Rayleigh scatter can improve spatial resolution in some cases by providing strain information at every location in the core. A further advantage with using Rayleigh scatter is that the fiber can be interrogated by a laser at any wavelength, and not necessarily one centered on the wavelength that a Bragg grating happens to be written at. Rayleigh scatter also provides an unambiguous identification of each segment of fiber. In cases where long lengths (e.g., long is only a few meters) of fiber must be measured, multipath reflections in even very weak Bragg gratings can corrupt the strain measurements at distant locations in the fiber. The appropriate embodiment of the sensing mechanism depends on the specific application.

Referring back to FIG. 1, the multi-core optical fiber 20 is coupled to single core optical fibers 55, 57 through a coupling device 25. FIGS. 3 and 4 shows an embodiment of the invention where three single core optical fibers 55, 57, 59 are coupled to the multi-core optical fiber 20 through a coupling device 25. The figures depict non-limiting, example embodiments where each single core optical fiber 55, 57 (in FIGS. 1 and 2) or 55, 57, 59 (in FIGS. 3 and 4) has a broadband reference reflector 60 positioned in relation to each strain sensor (again the scatter pattern of a segment of a fiber core corresponds to a strain sensor) to establish an optical path length for each reflector/strain sensor relationship. Nevertheless, the broadband reference reflector is optional and may be replaced with an internal reference path length.

An optical frequency domain reflectometer establishes a reference path. The optical frequency domain reflectometer 70 is coupled to the multi-core optical fiber 20 through the single core optical fibers 55, 57, 59 so that the frequency domain reflectometer 70 can receive signals from the fiber strain sensors. One example frequency domain reflectometer is the Luna Distributed Sensing System and is commercially available from Luna Innovations Incorporated. Another example of a commercially available OFDR system is the Optical Backscatter Reflectometer, also available from Luna Innovations.

Figure 5:
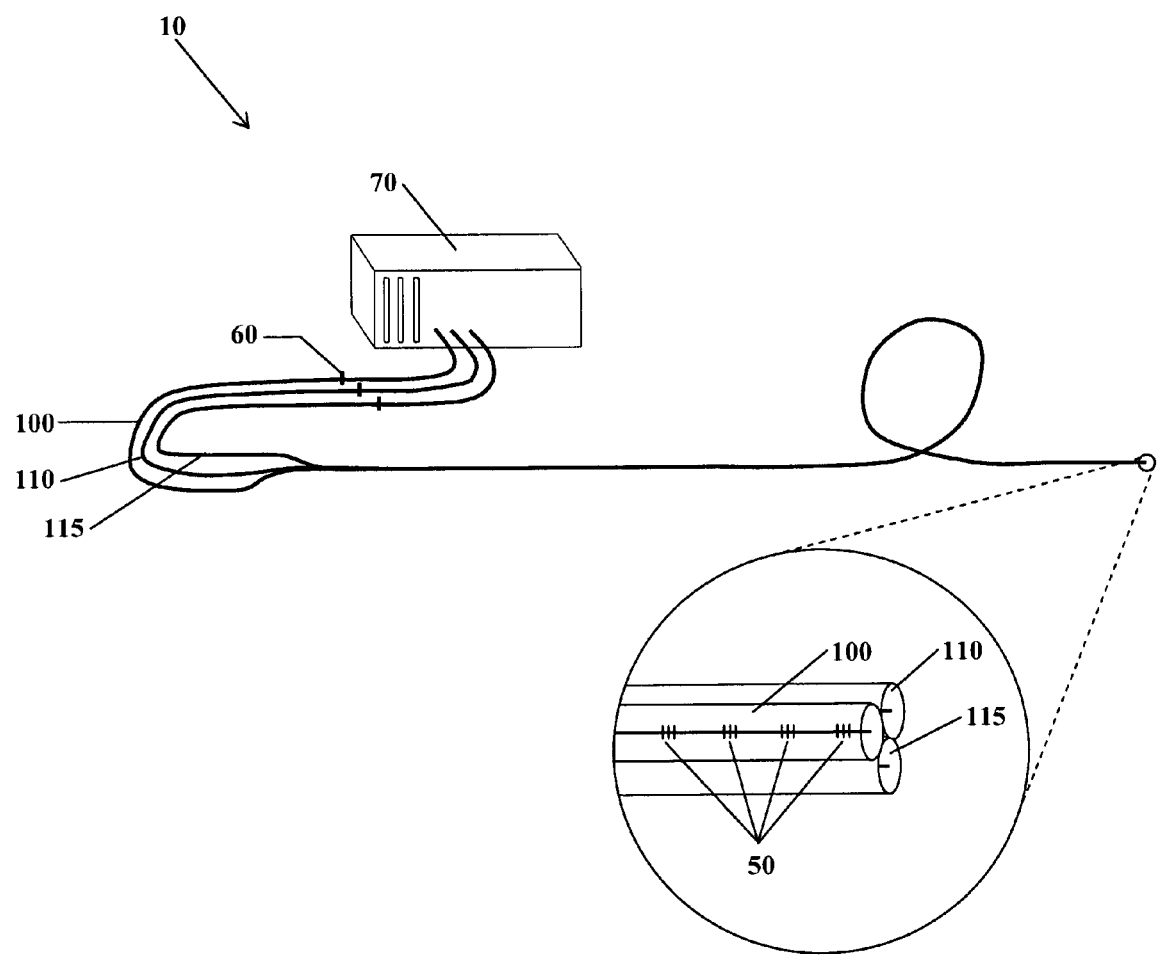
FIG. 5 depicts an example embodiment where the optical fiber includes three single core optical fibers with Bragg gratings.
Figure 6:
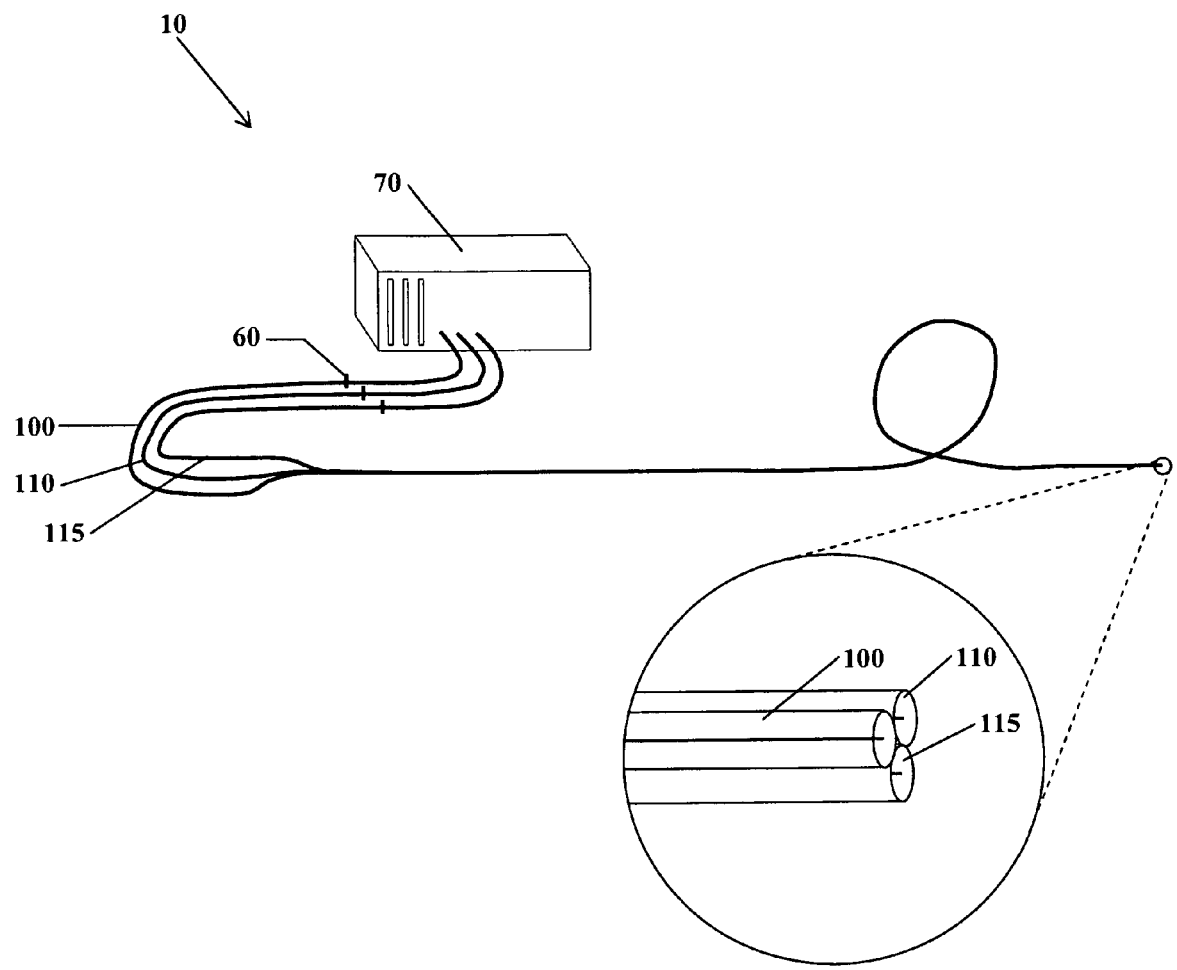
FIG. 6 depicts a preferred example embodiment where the optical fiber includes three single core optical fibers and the sensing mechanism is Rayleigh scatter.

FIGS. 5 and 6 depict an alternative non-limiting example embodiment where the optical fiber includes is at least two single core optical fibers and, preferably, three single core optical fibers 100, 110, 115. When three single core optical fibers are used, the fiber cores are non-coplanar and preferably from a triangular shape. The triangular shape can be such that each fiber core has a center, and each center is 120° with respect to each of the other two core centers. The 120° relationship helps to reduce distortions. As with the multi-core optical fiber, the fiber cores are spaced apart such that mode coupling between the fiber cores is reduced and preferably minimized Also, as seen in the multi-core optical fiber in FIG. 5, multiple of Bragg gratings 50 are disposed within each fiber core. In FIG. 6 the intrinsic Rayleigh scatter of the fiber core is the sensing mechanism, In one preferred example embodiment, an optional broadband reference reflector 60 is used to establish an optical path length for each reflector/strain sensor relationship. A frequency domain reflectometer 70 is coupled to transmit light to and receive reflected light from the single core optical fibers.

Figure 7:
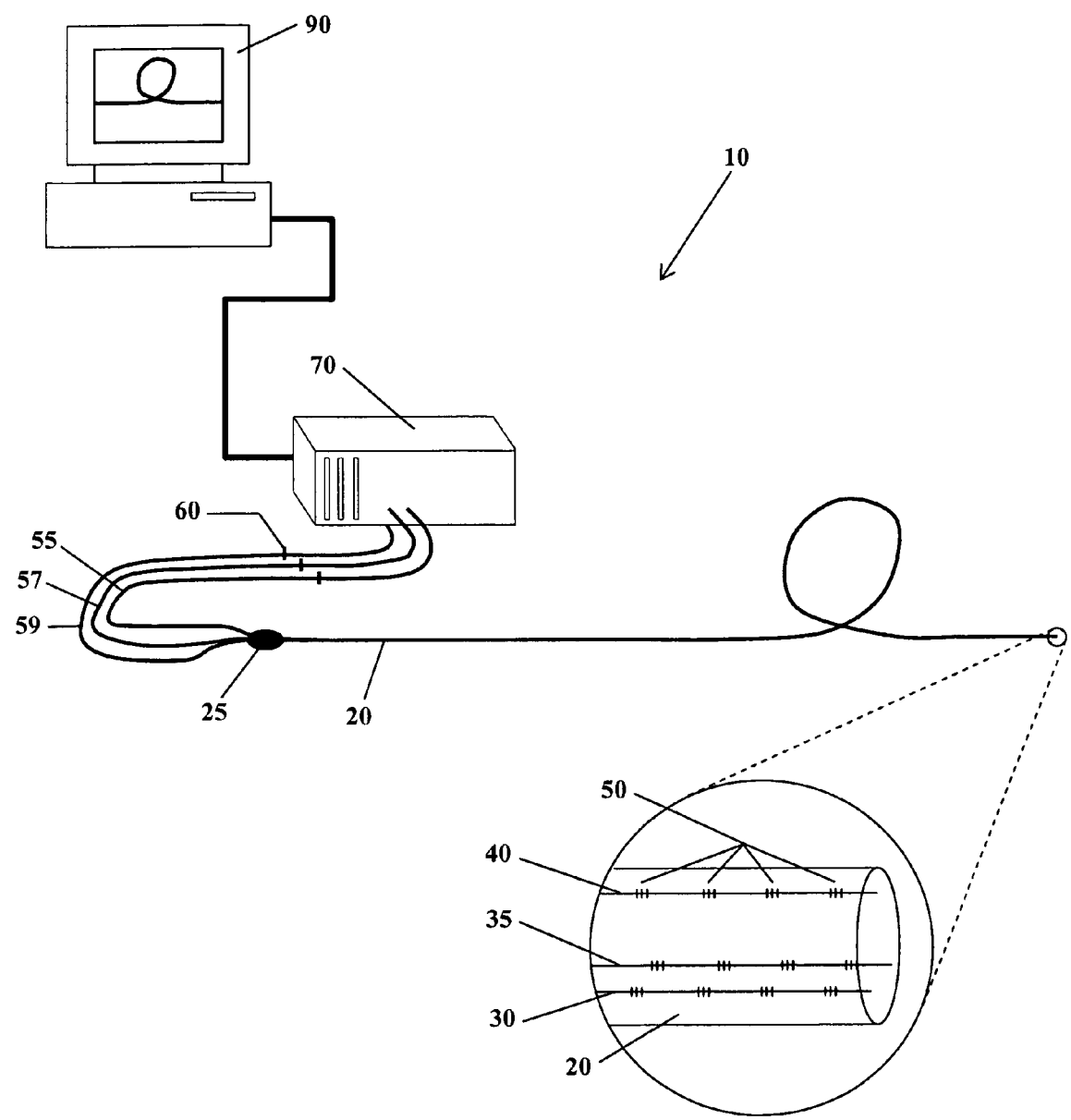
FIG. 7 is a schematic representation of an optical arrangement for the fiber optic position and/or shape sensing device with Bragg gratings.
Figure 8:
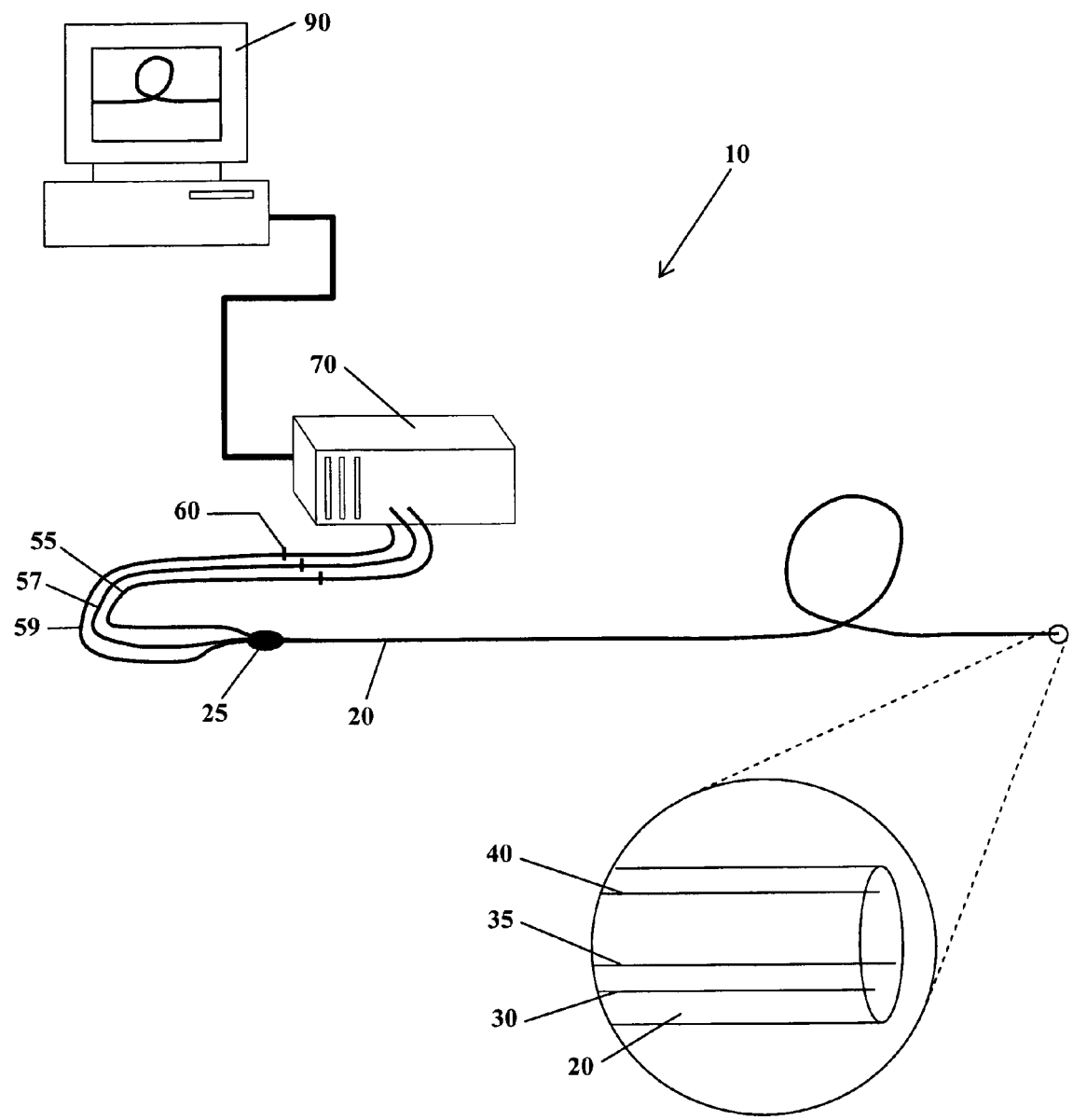
FIG. 8 is a schematic representation of an optical arrangement for the fiber optic position and/or shape sensing device where the sensing mechanism is Rayleigh scatter.

In a further non-limiting example embodiment shown in FIGS. 7 and 8, the fiber optic position and shape sensing device 10 has a computer 90 coupled to the frequency domain reflectometer 70. It is understood that the optical arrangement shown in FIGS. 7 and 8 is not limited to those devices employing multi-core optical fibers but that it may be used in combination with those devices employing single core optical fibers as well. The computer 90 correlates the signals received from the frequency domain reflectometer 70 to strain measurements. These strain measurements are correlated into local bend measurements. A local bend measurement is defined as the bend between a reference strain sensor and the next set of strain sensors along the fiber. The local bend measurements are integrated into a position or shape. If the optical fiber has only two cores, then shape determination is limited to two dimensions, if there are three or more cores, three dimensional shape is determined, and in both instances, position is determined. It is also understood that the operations performed by the computer 90 could be performed in the OFDR 70, if desired.

The technology effectively determines the shape of an object by measuring the shape of the optical fiber. Examples of various objects include but are not limited to: a position tracking device, such as a robot, and flexible objects such as medical instruments or flexible structures. Based on these measurements, relative position of a portion of the object is also ascertainable. For example, shape sensing is accomplished using multiple Rayleigh scatter patterns associated with fiber core segments located near the shape of to be sensed. Assuming each sensor segment is sufficiently small to achieve the desired spatial resolution, by detecting a curvature of the object at each individual sensor segment, the overall shape is reconstructed through an integration process.

To monitor the shape of an object that can deform in three dimensions, a measure of a 3-dimensional "vector" strain is required. Three or more cores are used, with each core containing multiple strain sensors (preferably one hundred (100) or more). Preferably, each sensor is collocated in the axial dimension. Three optical fiber cores are fixed together such that their centers are non-coplanar. Preferably, the core centers are each 120° with respect to each of the other two core centers and form a triangular shape. Any number of optical fiber cores greater than three can also be used for three dimensional bend sensing. The separate cores of the optical fiber are embedded into a monolithic structure. By co-locating strain sensors along the length of the fiber to create multiple distributed sensing points, the differential strain between the cores is used to calculate curvature along the length of the fiber. Based on the curvature of the fiber at individual sensing points, the overall shape of the fiber or at least a portion of the fiber may be reconstructed, presuming that each individual strain sensing point is sufficiently small.

Figure 9:
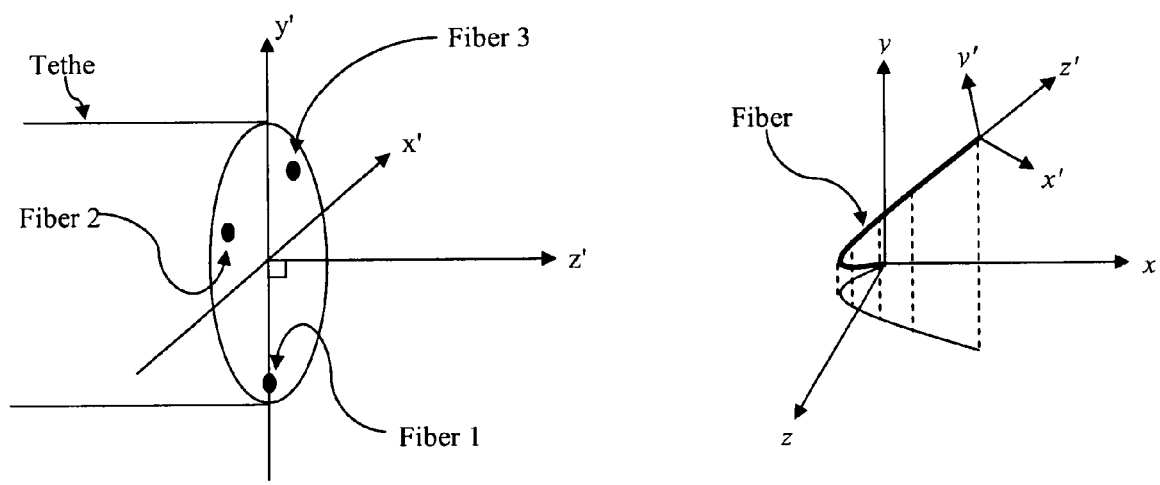
FIG. 9 depicts a sensor frame.

The fiber may be physically associated with an object, e.g., it can be inserted into, affixed to, aligned with, conformed to or otherwise follow the object. Strain values for each segment of a fiber physically associated with an object whose shape and/or position is(are) to be determined are used to compute a bend angle and bend radius for multiple fiber segments associated with at least a portion of the object shape and/or position is(are) to be determined. Starting from the beginning of the object (although not necessary), this data is used to compute the location of the next sensing triplet along the object and to define a new local coordinate system. An algorithm implemented on a computer interpolates circular arcs between each sensing triplet along the fiber in the region of interest. The geometry of the entire object may be determined by repeating the process for each sensing triplet along the length of the object. Since the fiber Bragg gratings or Rayleigh scatter pattern segments in each sensing fiber are collocated, a triplet of strain values at evenly-spaced segments along the object exists. For each step along the object, a local coordinate system (x', y', z') is defined called the sensor frame. This coordinate system has its origin at the center of the object's perimeter for any given sensing triplet. The z' axis points in the direction of the object, and the y' axis intersects with fiber 1. See FIG. 9 (the right part of the figure is an illustration of the fiber in a coordinate system).

Figure 10:
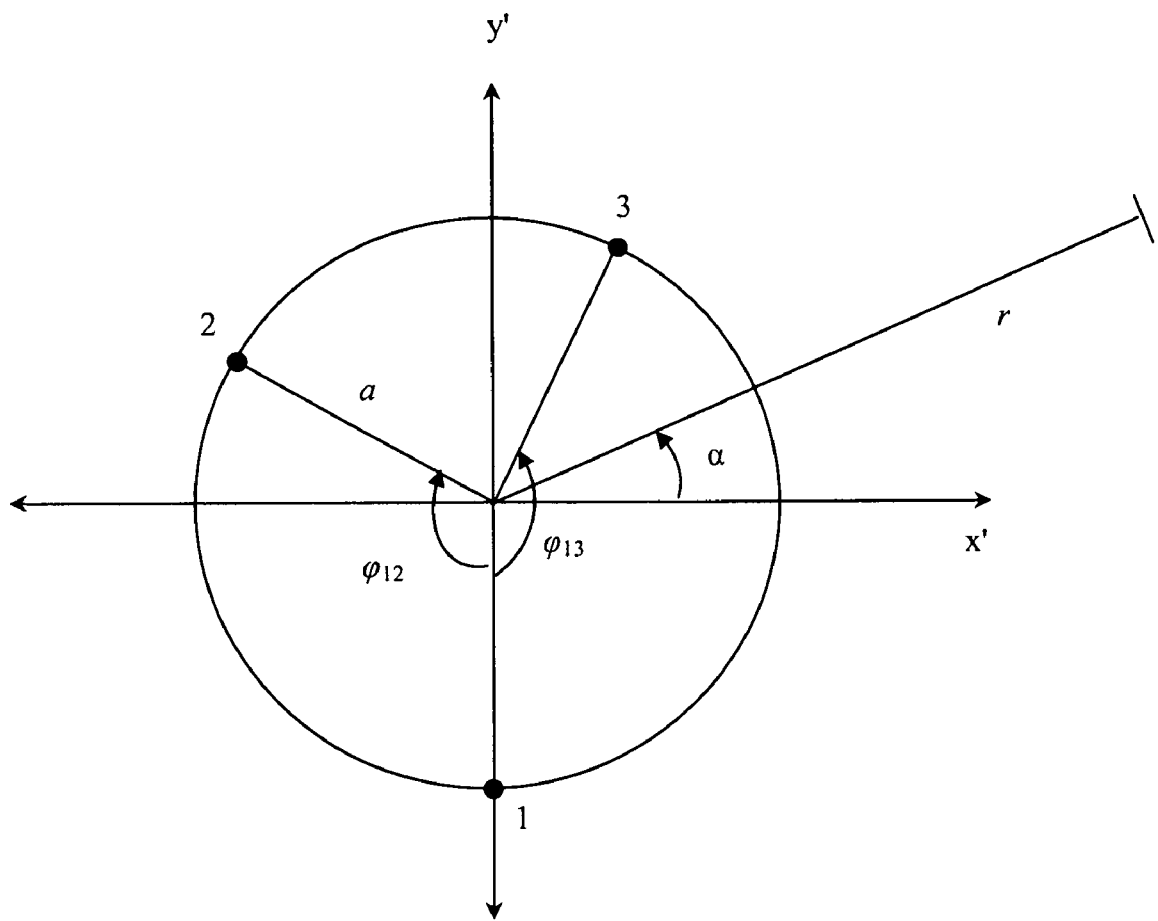
FIG. 10 is a bend parameter schematic.
Figure 11:
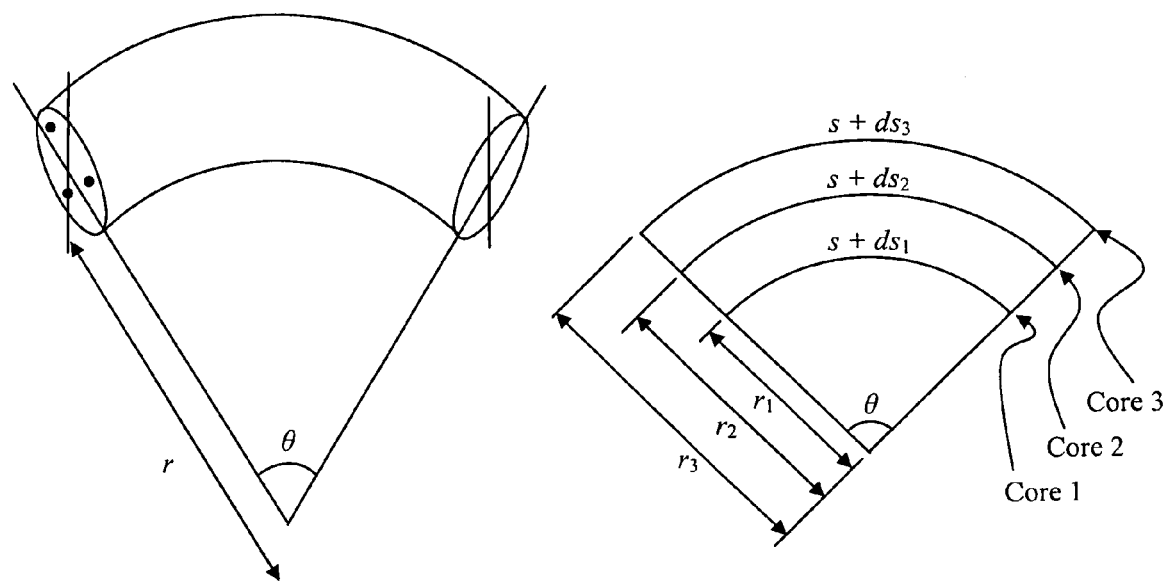
FIG. 11 depicts the bend geometry.

Using the three strain values ($\epsilon_1, \epsilon_2, \epsilon_3$) for a given sensing triplet, one can calculate the direction of the bend, $\alpha$, with respect to the x' axis as well as the bend radius, r, which is the distance from the center of curvature to the center of the core perimeter (see FIG. 10). Knowing r and $\alpha$ for a particular segment permits the computation of the coordinates of the end of the segment in the (x', y', z') coordinate system. The beginning of the fiber segment is taken to be the origin of the (x', y', z') system. When there is no curvature, each core segment has a length s. When a curvature is introduced, each core is generally a different distance ($r_1, r_2, r_3$) from the center of curvature, as shown in FIG. 11. Because all of the core segments subtend the same curvature angle, $\theta$, each segment must have a different length. The change in length due to bending the fiber is denoted as $ds_1$, $ds_2$ and $ds_3$ as shown in FIG. 11.

From the geometry shown in FIG. 1, the equations relating the change in length and radius of curvature of each fiber to the other fibers are derived as:

$$\theta = \frac{s + ds_1}{r_1} = \frac{s + ds_2}{r_2} = \frac{s + ds_3}{r_3} \quad (1)$$

Since strain (denoted by $\epsilon$) is defined as the ratio of the change in length of the fiber, ds to its unstretched length s (i.e., $\epsilon = ds/s$) the first part of Equation 1 is written in terms of the measured strains.

$$\theta = \frac{s + ds_1}{r_1} = s\left(\frac{1 + ds_1/s}{r_1}\right) = s\left(\frac{1 + \varepsilon_1}{r_1}\right) \quad (2)$$

Extending this argument to the other terms of Equation 1 the following expression results:

$$\frac{1 + \varepsilon_1}{r_1} = \frac{1 + \varepsilon_2}{r_2} = \frac{1 + \varepsilon_3}{r_3} \quad (3)$$

Figure 12:
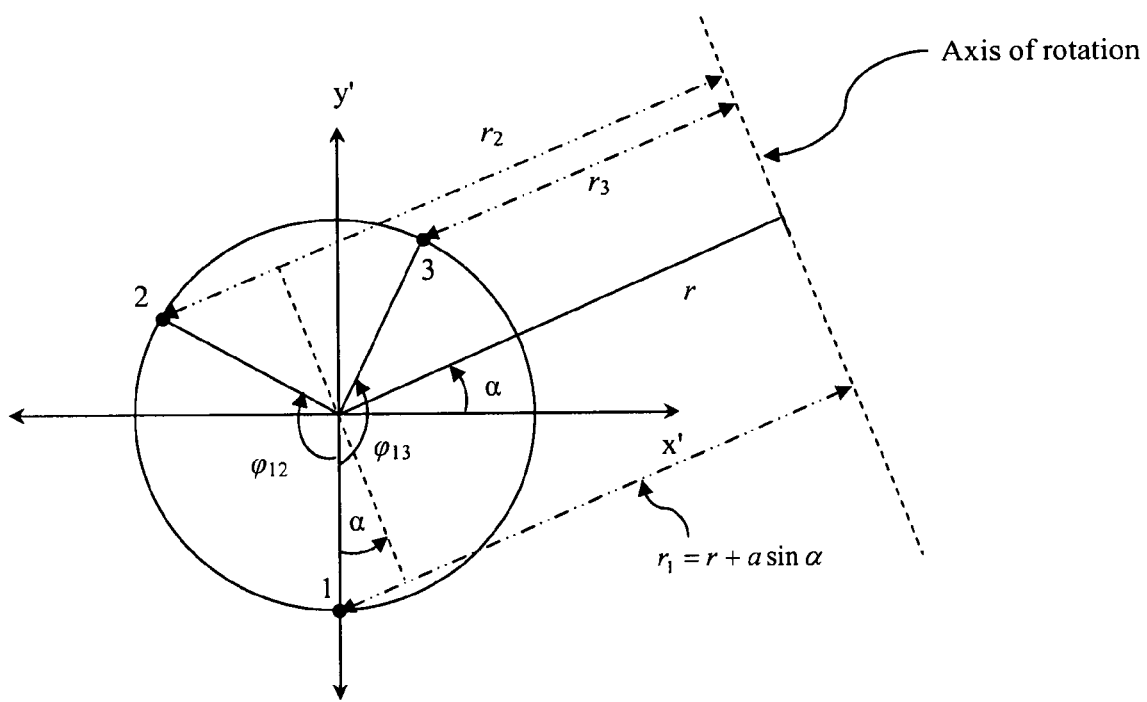
FIG. 12 shows the fiber cross-section geometry.

In order to solve Equation 3 for r and $\alpha$, $r_1$, $r_2$, and $r_3$ need to be written in terms of r and $\alpha$. This can be done by analyzing the geometry of the fiber cross-section (FIG. 12) and results in the following expressions for the radii of curvature for each of the fiber cores:

$r_1 = r + a \sin \alpha$ $r_2 = r + a \sin(\alpha + \phi_{12})$ $r_3 = r + a \sin(\alpha - \phi_{13})$ \quad (4)

Using Equations 4 to make substitutions in Equation 3 the following three equations are derived for r and $\alpha$. These equations are:

$(1+\epsilon_1)(r+a \sin(\alpha+\phi_{12}))=(1+\epsilon_2)(r+a \sin(\alpha))$ $(1+\epsilon_1)(r+a \sin(\alpha-\phi_{13}))=(1+\epsilon_3)(r+a \sin(\alpha))$ $(1+\epsilon_2)(r+a \sin(\alpha-\phi_{13}))=(1+\epsilon_3)(r+a \sin(\alpha+\phi_{12}))$ \quad (5)

In order to make these equations easier to follow the following substitutions are made.

$\epsilon_{12}=\epsilon_2-\epsilon_1 \quad \epsilon_{13}=\epsilon_3-\epsilon_1 \quad \epsilon_{23}=\epsilon_3-\epsilon_2$ $\sigma_1=1+\epsilon_1 \quad \sigma_2=1+\epsilon_2 \quad \sigma_3=1+\epsilon_3$ \quad (6)

Algebraically, the following solution is found for $\alpha$.

$$\tan\alpha = \frac{\varepsilon_{13}\sin\varphi_{12} + \varepsilon_{12}\sin\varphi_{13}}{\varepsilon_{23} - \varepsilon_{13}\cos\varphi_{12} + \varepsilon_{12}\cos\varphi_{13}} \quad (7)$$

It is clear from Equation 7 that the bend angle, $\alpha$, is dependent only on the differential strains, not the absolute strain values. The bend radius r can be computed in three different ways. Each of these formulae give the same solution for r, but it is useful during implementation to have at least two handy in case one of the differential strains (defined in Equation 6) turns out to be zero.

$$r = \begin{cases} \frac{a}{\varepsilon_{12}}(\sigma_1 \sin(\alpha + \varphi_{12}) - \sigma_2 \sin(\alpha)) \\ \frac{a}{\varepsilon_{13}}(\sigma_1 \sin(\alpha - \varphi_{13}) - \sigma_3 \sin(\alpha)) \\ \frac{a}{\varepsilon_{23}}(\sigma_2 \sin(\alpha - \varphi_{13}) - \sigma_3 \sin(\alpha + \varphi_{12})) \end{cases} \quad (8)$$

Equation 7 shows that $-\pi/2 < \alpha < \pi/2$. The extra $\pi$ radians appear in the r calculation. That is, if r is negative, simply negate r and add $\pi$ to $\alpha$. After this operation, r>0 and $0 \leq \alpha < 2\pi$. Also, when implementing an algorithm, cases where $\epsilon_1 = \epsilon_2 = \epsilon_3$ form a special case where the bend angle is arbitrary because the bend radius is infinite (zero curvature).

EXAMPLES

Example 1

The optical fiber includes three single core optical fibers. Shape sensors were surface attached to the outside of an inflatable isogrid boom that was approximately 1.2 m in length. The fiber optic sensor arrays, each containing approximately 120 sensors with a 0.5 cm gauge length spaced at 1 cm intervals, center-to-center, ran along the entire axial length of the boom oriented 120° with respect to each other. The boom was fixed at one end while the other end was unattached in a classic cantilever beam set-up. Various weights were then placed on the free-floating end while strain measurements were taken to monitor the dynamic shape of the structure. A standard height gauge was used to directly measure the deflection of the end of the boom for the purposes of data correlation. Upon comparison of the data, there was an excellent correlation between the fiber optic shape sensors and the height gauge. With a mass of 2.5 kg suspended from the end, the height gauge indicated a deflection of 1.7 mm while the fiber optic shape sensors indicated a deflection of 1.76 mm; with a mass of 4 kg suspended from the end, the height gauge indicated a deflection of 2.7 mm while the fiber optic shape sensors indicated a deflection of 2.76 mm.

Example 2

Figure 13:
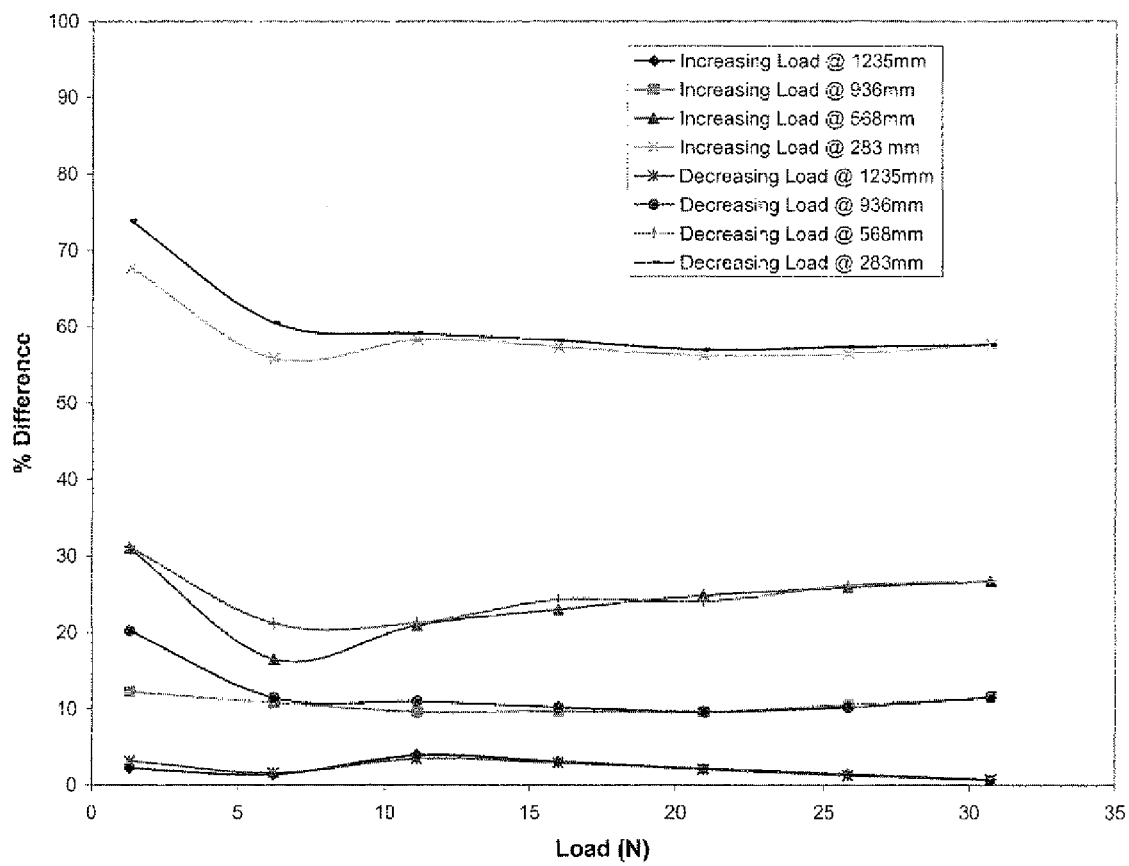
FIG. 13 is a graphical representation of the percent error between the laser displacement sensors and the fiber optic shape sensors.

An isogrid boom was fixed at one end while the other end was unattached in a classic cantilever beam set-up. Various weights were then placed on the free-floating end while measurements were taken to monitor the shape/relative position of the structure using the fiber optic position and shape sensing device of the present invention. Laser displacement sensors at four locations were suspended above the boom to directly measure the deflection of the boom for the purposes of data correlation. Table 1 shows the percent error between the laser displacement sensors and fiber optic shape sensors. This data is depicted graphically in FIG. 13.

TABLE 1

| | Sensor Location (mm) | | | |
|---|---|---|---|---|
| Load (g) | 1235 | 936 | 568 | 283 |
| 0 | | | | |
| 132 | 2.19 | 12.2 | 31.0 | 67.7 |
| 623 | 1.34 | 10.8 | 16.5 | 55.8 |
| 1132 | 3.91 | 9.56 | 21.0 | 58.3 |
| 1632 | 3.09 | 9.64 | 23.0 | 57.4 |
| 2132 | 2.13 | 9.55 | 24.8 | 56.2 |
| 2632 | 1.40 | 10.5 | 25.9 | 56.5 |
| 2132 | 2.05 | 9.58 | 24.0 | 57.0 |
| 1632 | 2.90 | 10.2 | 24.3 | 58.2 |
| 1132 | 3.45 | 10.9 | 21.3 | 59.2 |
| 632 | 1.56 | 11.4 | 21.2 | 60.5 |
| 132 | 3.19 | 20.2 | 31.2 | 73.9 |
| 0 | | | | |
| Average | 2.24 | 11.2 | 24.4 | 59.7 |

At each load, anywhere from 127 to 192 measurements were taken using the Luna Distributed Sensing System unit commercially available from Luna Innovations Incorporated. The standard deviations of the shape data for each load at the same four points along the tether showed that in the worst case, the standard deviation is 14 μm, indicating a very high degree of reproducibility.

Example 3

An oscillator (LDS v-203 electrodynamic shaker) driven by a function generator and amplified by a power amplifier was attached to the free end of an isogrid boom which was attached in a classic cantilever beam configuration. A sinusoidal signal was used to drive the shaker with a displacement amplitude of roughly 1.6 mm, peak-to-peak (0.566 RMS) and frequencies of 0.5 and 1.0 Hz. The fiber optic position and shape sensing device of the present invention was attached to the isogrid boom and was used to capture dynamic shape data at roughly 2.189 Hz. Using the dynamic shape data captured by the sensing device while the beam was oscillating, modal analysis was performed. Approximately 2853 samples were taken at the 0.5 Hz oscillation mode. The frequency of oscillation was pinpointed to within roughly ±0.0004 Hz. The 1.0 Hz oscillation mode was sampled 240 times, yielding an accuracy of approximately ±0.0046 Hz. The results of this test show that the fiber optic position and shape sensing device is useful to characterize the dynamic performance of a mechanical structure.

Example 4

A series of shape measurements of a 3 m long vertically suspended isogrid boom were performed. The fiber optic position and shape sensing device, containing approximately 300 fiber Bragg grating sensors in each of 3 cores with a 0.5 cm gauge length spaced at 1 cm intervals, center-to-center, were positioned along the outside surface of the boom along the entire axial length oriented 120° with respect to each other. The measurements included cantilever bending, axial loading, and dynamic bending (approximately 5 Hz). Comparisons were made with a deflection gauge and were found to correlate to within ±0.5 mm over the full length of the isogrid boom.

The fiber optic position and/or shape sensing device is useful for providing practical shape and/or relative position sensing over extended lengths. The combination of high spatial resolution achieved through multiple strain measurements of the fiber obtained from corresponding Rayleigh backscatter measurements coupled with non-rigid attachment to the object enables higher accuracy than systems described in the background. In particular, systems using wave division multiplexing coupled with fiber Bragg gratings are limited in range or have the inability to achieve high spatial resolution. Systems where cross-talk or mode coupling occurs between the fiber cores are difficult to implement because such arrangements are subject to measurement distortions. Nor are models required of the mechanical behavior of the object in order to determine the position or shape of the object. Putting Bragg gratings into a fiber is expensive and difficult, and, in the case of certain metal coated fibers, impossible. Therefore, Rayleigh-based sensing adds significant advantage in terms of the availability and cost of multi-core fiber. It also dispenses with the necessity to match the laser scanning wavelength range with the gratings that are written into the fiber. Moreover, with Rayleigh scatter-based sensing, every location along the fiber is a sensing region.

The fiber optic position and/or shape sensing device has many applications, a few example of which are identified below. It may be used to monitor true deflection of critical structures as well as the shape of structures. The sensing device serves as a feedback mechanism in a control system. The device is suitable for use as a monitor for the relative position of an object attached to it. Another application is to attach the device to a search and rescue robot in places where global positioning system (GPS) either possesses insufficient resolution or is unavailable. Alternatively, the device may be attached to a floating buoy deployed by a ship to make differential GPS measurements. The device may be used for performing modal analysis of mechanical structures. The device is also suitable for medical applications such as minimally invasive surgical techniques as well as biometric monitoring. For example, the shape or position of medical devices or instruments such as catheters and colonoscopes could be determined with sufficient precision as to yield useful information to an end-user or to a control system.

Figure 14:
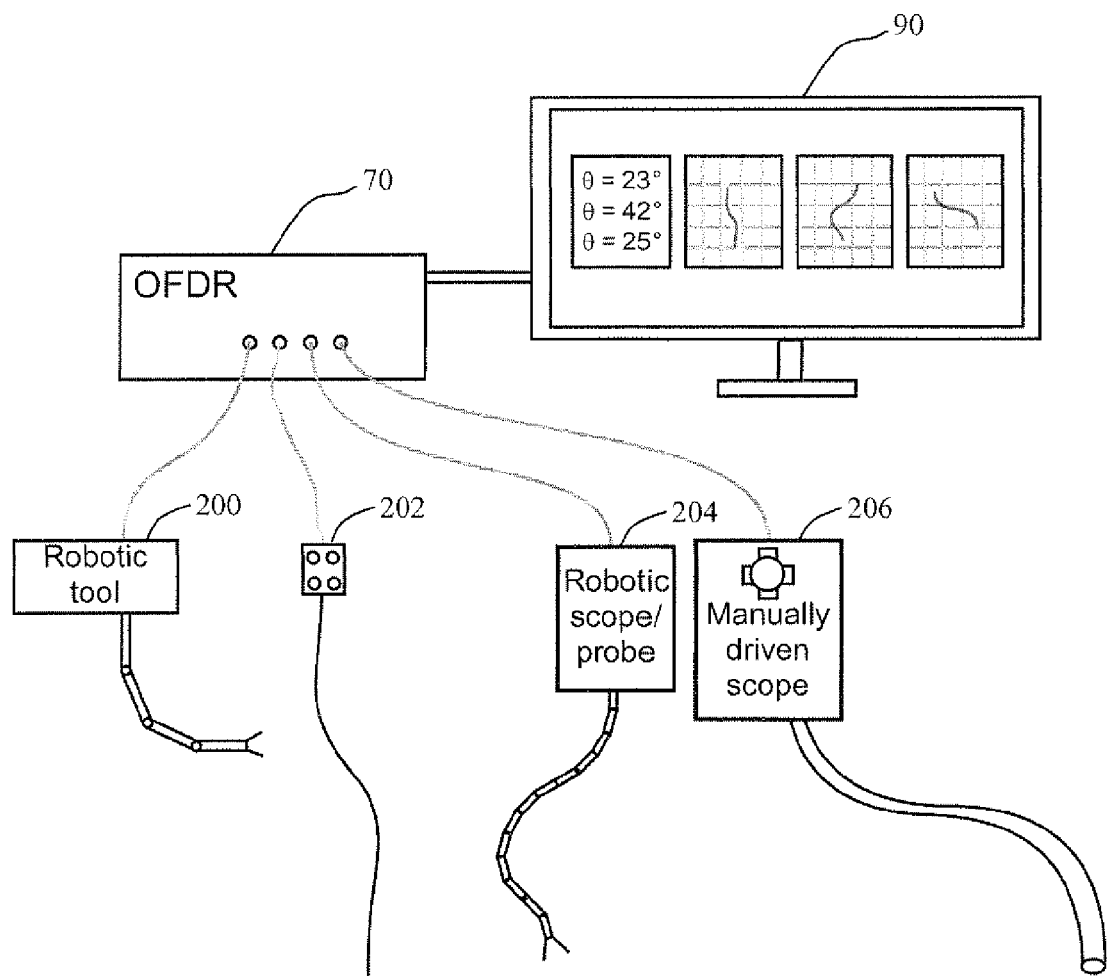
FIG. 14 is a schematic representation of various example medical applications for the optical technology described in this application.

FIG. 14 is a schematic representation of non-limiting example medical applications for the optical technology described in this application. Of course, the medical applications are examples only, and they are not limited to those shown. An OFDR 70 is coupled to a computer 90 to display various information related to strain, position, and/or shape of a desired portion of one or more optical fibers associated with one or more medical instruments. Example medical instruments illustrated include a precision, robotically-driven manipulator tool 200, a flexible catheter 202, a segmented, robotically-driven scope or probe 204, and a manually-driven scope 206 such as a colonoscope. Each medical instrument 200, 202, 204, and 206 is physically associated in some fashion with an optical fiber that is coupled to the OFDR 70. For example, each optical fiber may be disposed in, affixed to, coupled with, or conforming to at least a portion of the elongate body of its medical instrument. Other physical associations are possible to permit the optical fiber to determine a position and/or shape of a portion of the instrument. Knowing the position and/or shape of a portion of the medical instrument can be very valuable in medical procedures.

For each optical fiber, the OFDR 70 obtains a Rayleigh scatter pattern associated with each of multiple fiber segments (from each core if the fiber includes multiple cores) and using the Rayleigh scatter patterns to determine a strain parameter of each of the multiple fiber segments. A position and/or shape of the object is determined by the computer 90 based on the determined strain parameters. The computer 90, in one example implementation, translates the strain parameters to local bend measurements corresponding to a bend in the object and integrates the local bend measurements to determine the position or shape of the object at the bend.

Although various example embodiments have been shown and described in detail, the claims are not limited to any particular embodiment or example. None of the above description should be read as implying that any particular element, step, range, or function is essential such that it must be included in the claims scope. Reference to an element in the singular is not intended to mean "one and only one" unless explicitly so stated, but rather "one or more." The scope of patented subject matter is defined only by the claims. The extent of legal protection is defined by the words recited in the allowed claims and their equivalents. All structural and functional equivalents to the elements of the above-described example embodiments that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. No claim is intended to invoke paragraph 6 of 35 USC §112 unless the words "means for" or "step for" are used. Furthermore, no feature, component, or step in the present disclosure is intended to be dedicated to the public regardless of whether the feature, component, or step is explicitly recited in the claims.

The invention claimed is:

1. A fiber optic sensing device comprising:
an optical fiber including at least two fiber cores spaced apart so that mode coupling between the fiber cores is reduced;
wherein each fiber core has an associated Rayleigh scatter signature and different segments of each fiber core correspond to a portion of the associated Rayleigh scatter signature;
a frequency domain reflectometer coupled to the optical fiber configured to obtain a Rayleigh scatter pattern associated with each of multiple fiber segments from each core; and
a computing device configured to determine a spectral shift of the Rayleigh scatter pattern associated with each of multiple fiber segments from each core and to use the determined spectral shift for the Rayleigh scatter pattern associated with each of multiple fiber segments from each core in determining a strain parameter for each of the multiple fiber segments from each core and in determining a position and/or shape of a portion of the fiber based on the determined strain parameters.

2. A fiber optic sensing device according to claim 1, wherein the frequency domain reflectometer is configured to detect a distributed strain field along a portion of each core including multiple segments based on the obtained Rayleigh scatter pattern associated with each of those multiple fiber segments.

3. A fiber optic sensing device according to claim 1, wherein the optical fiber includes at least two single core optical fibers, and wherein the frequency domain reflectometer is configured to detect a distributed one-dimensional strain field along a portion of each of the two single core optical fibers including multiple segments based on the obtained Rayleigh scatter pattern associated with each of those fiber segments.

4. A fiber optic sensing device according to claim 1, wherein the optical fiber includes three single core optical fibers, wherein the three fiber cores are non-coplanar and form a triangular shape, and wherein the frequency domain reflectometer is configured to detect a distributed strain field along a portion of each of the three single core optical fibers including multiple segments based on the obtained Rayleigh scatter pattern associated with each of those fiber segments.

5. A fiber optic sensing device according to claim 4, wherein the three fiber cores each have a center, and wherein each center is 120° with respect to each of the other two core centers.

6. A fiber optic sensing device according to claim 1, wherein the frequency domain reflectometer is configured to obtain at least one hundred independent strain measurements along the length of the core.

7. A fiber optic sensing device according to claim 1, wherein the optical fiber is a multicore optical fiber that comprises at least three fiber cores.

8. A fiber optic sensing device according to claim 7, wherein the three fiber cores are non-coplanar and form a triangular shape.

9. A fiber optic sensing device according to claim 8, wherein the three fiber cores each have a center, wherein each center is 120° with respect to each of the other two core centers.

10. A fiber optic sensing device according to claim 1, wherein the frequency domain reflectometer includes a reference reflector, and wherein the frequency domain reflectometer is configured to obtain Rayleigh scatter patterns to establish an optical path length between the reference reflector and the segments corresponding to the obtained Rayleigh scatter patterns.

11. A fiber optic sensing device according to claim 10, wherein the computing device is configured to convert the strain parameters into local bend measurements defining a bend in the fiber at a particular location along the fiber and integrate the local bend measurements into a position or a shape at the particular location along the fiber.

12. A fiber optic sensing device according to claim 1 disposed in, affixed to, coupled with, or conforming to at least a portion of an elongated body whose position and/or shape is to be determined.

13. A fiber optic sensing device according to claim 12, wherein the elongated body is a catheter, tube, pipe, sleeve, instrument, tool, wire, line, cavity, vessel, lumen, or conduit.

14. A fiber optic sensing device according to claim 1, wherein the computing device is configured to determine the position and/or a shape of the portion of the object based on the determined strain parameters without using a sensing element coupled optically or written onto each of the fiber cores.

15. A fiber optic sensing device according to claim 1, wherein the computing device is configured to use a cross correlation to calculate the spectral shift of the Rayleigh scatter patterns to determine a strain parameter for each of the multiple fiber segments from each core.

16. A fiber optic sensing device according to claim 1, wherein the cross correlation is a cross correlation of the amplitude of the Fourier transform of the complex data associated with the Rayleigh scatter for each fiber segment.

17. A fiber optic method, comprising:
coupling a frequency domain reflectometer to an optical fiber having at least two fiber cores spaced apart so that mode coupling between the fiber cores is reduced, wherein each fiber core has an associated Rayleigh scatter signature and different segments of each fiber core correspond to a portion of the associated Rayleigh scatter signature;
physically associating the optical fiber with a position and/or shape of an object;
using the frequency domain reflectometer to obtain a Rayleigh scatter pattern associated with each of multiple fiber segments from each core;
determining a spectral shift of the Rayleigh scatter pattern associated with each of multiple fiber segments from each core;
using the determined spectral shift for the Rayleigh scatter pattern associated with each of multiple fiber segments from each core in determining a strain parameter for each of the multiple fiber segments from each core; and
determining a position and/or shape of the object based on the determined strain parameters.

18. A fiber optic method according to claim 17, further comprising:
translating the strain parameters to local bend measurements corresponding to a bend in the object; and
integrating the local bend measurements to determine the position or shape of the object at the bend.

19. A fiber optic method according to claim 17, wherein the object is a position tracking device.

20. A fiber optic method according to claim 17, wherein the position and/or a shape of the portion of the object is determined based on the determined strain parameters without using a sensing element coupled optically or written onto each of the fiber cores.

21. A fiber optic method according to claim 17, wherein the optical fiber comprises three cores and wherein the object has a three dimensional shape.

22. A fiber optic method according to claim 17, wherein the object is a flexible object.

23. A fiber optic method according to claim 22, wherein the flexible object is a medical instrument or a flexible structure.

24. A fiber optic method according to claim 17, further comprising using a cross correlation to calculate the spectral shift of the Rayleigh scatter patterns to determine a strain parameter for each of the multiple fiber segments from each core.

25. A fiber optic method according to claim 17, wherein the cross correlation is a cross correlation of the amplitude of the Fourier transform of the complex data associated with the Rayleigh scatter for each fiber segment.

26. A medical instrument system, comprising:
a medical instrument;
an optical fiber conforming at least in part to at least a portion of a shape of the medical instrument and including at least two fiber cores spaced apart so that mode coupling between the fiber cores is reduced;
wherein each fiber core has an associated Rayleigh scatter signature and different segments of each fiber core correspond to a portion of the associated Rayleigh scatter signature;
a frequency domain reflectometer coupled to the optical fiber configured to obtain a Rayleigh scatter pattern associated with each of multiple fiber segments from each core that is associated with the portion of the shape of the medical instrument; and
a computing device configured to determine a spectral shift of the Rayleigh scatter pattern associated with each of multiple fiber segments from each core and to use the determined spectral shift for the Rayleigh scatter pattern associated with each of multiple fiber segments from each core in determining a strain parameter for each of the multiple fiber segments from each core and in determining a position and/or a shape of the portion of the medical instrument based on the determined strain parameters.

27. The medical instrument system in claim 26, wherein the medical instrument includes an elongate instrument body.

28. The medical instrument system in claim 27, wherein the elongate body is a catheter, tube, pipe, sleeve, instrument, tool, wire, line, cavity, vessel, lumen, or conduit.

29. The medical instrument system in claim 28, wherein the elongate body is flexible.

30. The medical instrument system in claim 26, wherein the computing device is configured to determine the position and/or a shape of the portion of the medical instrument based on the determined strain parameters without using a sensing element coupled optically or written onto each of the fiber cores.

31. The medical instrument system in claim 26, wherein the medical instrument is a robot.

32. The medical instrument system in claim 26, wherein the optical fiber comprises three cores, and wherein the medical instrument has a three dimensional shape.

33. The medical instrument system in claim 26, wherein the computing device is configured to convert the strain parameters into local bend measurements defining a bend in the fiber at a particular location along the fiber and integrate the local bend measurements into a position or a shape at the particular location along the fiber.

34. The medical instrument system in claim 26, wherein the computing device is configured to use a cross correlation to calculate the spectral shift of the Rayleigh scatter patterns to determine a strain parameter for each of the multiple fiber segments from each core.

35. The medical instrument system in claim 26, wherein the cross correlation is a cross correlation of the amplitude of the Fourier transform of the complex data associated with the Rayleigh scatter for each fiber segment.

* * * * *